United States Patent
Minerath, III et al.

(10) Patent No.: US 7,066,006 B2
(45) Date of Patent: Jun. 27, 2006

(54) METHOD OF COLLECTING DATA RELATING TO ATTRIBUTES OF PERSONAL CARE ARTICLES AND COMPOSITIONS

(75) Inventors: Bernard J. Minerath, III, Oshkosh, WI (US); Elizabeth J. Buettner, Appleton, WI (US); Benjamin J. Kruchoski, Appleton, WI (US); Jason C. Cohen, Appleton, WI (US); Barry T. Reece, DeSoto, TX (US); Kimberly M. Geiser, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 311 days.

(21) Appl. No.: 10/188,416

(22) Filed: Jul. 2, 2002

(65) Prior Publication Data

US 2004/0003670 A1 Jan. 8, 2004

(51) Int. Cl.
*G01N 33/34* (2006.01)
*G01N 33/36* (2006.01)

(52) U.S. Cl. .............................. 73/7; 73/865.7; 73/866; 600/306; 600/557

(58) Field of Classification Search ................ 73/7, 73/432.1, 865.7, 866; 600/306, 557
See application file for complete search history.

(56) References Cited

U.S. PATENT DOCUMENTS

| | | | | |
|---|---|---|---|---|
| 4,300,981 A | * | 11/1981 | Carstens | 162/109 |
| 4,569,773 A | * | 2/1986 | Ramachandran et al. | 510/327 |
| 4,711,255 A | | 12/1987 | Syvarth et al. | |
| 4,734,162 A | | 3/1988 | Ampulski | |
| 4,771,381 A | | 9/1988 | Norman et al. | |
| 4,786,367 A | | 11/1988 | Bogart et al. | |
| 4,869,101 A | * | 9/1989 | Dvorsky | 73/159 |
| 4,882,221 A | | 11/1989 | Bogart et al. | |

(Continued)

FOREIGN PATENT DOCUMENTS

| | | | |
|---|---|---|---|
| EP | 0 373 974 A2 | | 6/1990 |
| JP | 11290315 | | 10/1999 |
| JP | 11344488 A | * | 12/1999 |
| JP | 2000093193 A | * | 4/2000 |
| WO | WO 99/12530 | | 3/1999 |
| WO | WO 00/37249 | | 6/2000 |
| WO | WO 00/59438 | | 10/2000 |
| WO | WO 01/74643 A1 | | 12/2000 |
| WO | WO 01/76842 A2 | | 10/2001 |
| WO | WO 02/03952 A2 | | 1/2002 |
| WO | WO 02/04917 A2 | | 1/2002 |
| WO | WO 02/31260 A2 | | 4/2002 |
| WO | WO 02/48457 A2 | | 6/2002 |
| WO | WO 02/057546 A1 | | 7/2002 |

OTHER PUBLICATIONS

Chambers, IV et al., "Sensory Testing Methodologies", 1996, ASTM, 2nd. edition, pp. 1–115.*
National Advertising Division Case Reports from Aug., 1999 p. 199–203.
Psychophysics: The Fundamentals; George A. Gescheider, 3rd Ed., pp. 183–191.

Primary Examiner—Hezron Williams
Assistant Examiner—David A. Rogers
(74) Attorney, Agent, or Firm—Senniger Powers

(57) ABSTRACT

Novel methods for measuring the soothing attributes of personal care compositions are disclosed. The methods disclosed are particularly suitable for measuring and comparing the soothing attributes of facial tissue to determine which facial tissue is most soothing to damaged skin. The methods include damaging the skin of a test subject to a predetermined amount, contacting a test facial tissue with the damaged skin, and rating the soothing attributes of the facial tissue. In a preferred embodiment, the amount of skin damage on the skin is determined by the test subject.

15 Claims, 5 Drawing Sheets

U.S. PATENT DOCUMENTS

| | | | |
|---|---|---|---|
| 4,943,350 A | | 7/1990 | Bogart et al. |
| 4,975,217 A | | 12/1990 | Brown-Skrobot et al. |
| 5,003,987 A | * | 4/1991 | Grinwald ................... 600/547 |
| 5,061,385 A | | 10/1991 | Duffin |
| 5,061,481 A | | 10/1991 | Suzuki et al. |
| 5,090,734 A | | 2/1992 | Dyer et al. |
| 5,338,407 A | * | 8/1994 | Dasgupta ................. 162/168.3 |
| 5,409,572 A | | 4/1995 | Kershaw et al. |
| 5,558,873 A | | 9/1996 | Funk et al. |
| 5,620,565 A | * | 4/1997 | Lazorisak et al. ............ 162/72 |
| 5,696,069 A | | 12/1997 | Ito et al. |
| 5,766,737 A | | 6/1998 | Willey et al. |
| 5,795,574 A | * | 8/1998 | Breton et al. ............... 424/115 |
| 5,871,763 A | | 2/1999 | Luu et al. |
| 5,885,415 A | | 3/1999 | Marinack et al. |
| 5,908,533 A | | 6/1999 | Marinack et al. |
| 5,919,750 A | | 7/1999 | Iacobucci |
| 6,027,610 A | * | 2/2000 | Back et al. ................. 162/111 |
| 6,074,527 A | * | 6/2000 | Hsu et al. .................. 162/111 |
| 6,146,648 A | | 11/2000 | Bret et al. |
| 6,171,442 B1 | | 1/2001 | Farrington, Jr. et al. |
| 6,176,972 B1 | | 1/2001 | Oriaran et al. |
| 6,179,961 B1 | | 1/2001 | Ficke et al. |
| 6,193,838 B1 | | 2/2001 | Oriaran et al. |
| 6,207,012 B1 | | 3/2001 | Oriaran et al. |
| 6,207,013 B1 | | 3/2001 | Oriaran et al. |
| 6,207,014 B1 | | 3/2001 | de Haut et al. |
| 6,248,211 B1 | | 6/2001 | Jennings et al. |
| 6,267,842 B1 | * | 7/2001 | Ona et al. ................... 162/135 |
| 6,294,186 B1 | | 9/2001 | Beerse et al. |
| 6,296,736 B1 | * | 10/2001 | Hsu et al. ................... 162/147 |
| 6,306,408 B1 | | 10/2001 | Eichhorn et al. |
| 6,340,677 B1 | * | 1/2002 | Nishimori et al. .......... 514/169 |
| 6,344,111 B1 | | 2/2002 | Wilhelm |
| 6,387,210 B1 | * | 5/2002 | Hsu et al. ...................... 162/4 |
| 6,419,789 B1 | | 7/2002 | Yeh et al. |
| 6,425,983 B1 | | 7/2002 | Marinack et al. |
| 6,500,894 B1 | * | 12/2002 | Lenti et al. ................. 524/507 |
| 6,528,121 B1 | * | 3/2003 | Ona et al. ................... 427/387 |
| 6,641,822 B1 | * | 11/2003 | Eichhorn et al. ............ 424/401 |
| 6,756,032 B1 | * | 6/2004 | Tepper et al. ................ 424/9.8 |
| 2003/0201085 A1 | * | 10/2003 | Vinson et al. ............... 162/204 |

\* cited by examiner

FIG. 1

SORENESS SCALE

INSTRUCTIONS: PLEASE PLACE A MARK ALONG THE SCALE WHICH BEST REPRESENTS THE DEGREE OF SORENESS YOU ARE EXPERIENCEING ON YOUR NOSE

CYCLE = 1

| 0 | 1 | 2 | 3 |
|---|---|---|---|
| NO SORENESS | SLIGHTLY OR MILDLY SORE | MODERATELY SORE | EXTREMELY SORE |

SUBJECT'S SIGNATURE: _____ TECHNICIAN'S SIGNATURE: _____

DATE: _____ DATE: _____

COMMENTS

FIG. 2

SOOTHING SCALE

INSTRUCTIONS: PLEASE PLACE A MARK ALONG THE SCALE WHICH BEST REPRESENTS HOW SOOTHING THIS TISSUE IS TO YOUR NOSE.

CYCLE = 1

| 0 | 1 | 2 | 3 |
|---|---|---|---|
| NOT SOOTHING | MILDLY SOOTHING | MODERATELY SOOTHING | VERY SOOTHING |

SUBJECT'S SIGNATURE: _____  TECHNICIAN'S SIGNATURE: _____
DATE: _____  DATE: _____

COMMENTS

METHOD OF COLLECTING DATA RELATING TO ATTRIBUTES OF PERSONAL CARE ARTICLES AND COMPOSITIONS

BACKGROUND OF THE INVENTION

The present invention relates to collecting data relating the ability of personal care compositions to soothe damaged skin. This method can also be used to measure other perceptual attributes that are defined by an individual's internal construct. These perceptual attributes include, but are not limited to, soothing, calming, relaxing, relieving, or pleasantness. More particularly, the present invention relates to an in vivo method of quickly and accurately measuring the soothing ability of a personal care composition, such as, for example, a facial tissue. The methods described herein allow for clinical studies and direct comparisons of different personal care compositions for determining the relative abilities of the products to deliver soothing attributes or beneficial perceptual changes to damaged skin, and are particularly well suited for determining the soothing attributes of facial tissue.

In today's marketplace, there are a wide variety of personal care compositions available to the consuming public. Regarding facial tissues alone, there are several brand-name and generic choices for consumers. Because the marketplace is crowded and competitive, companies seek to promote their respective brands by making certain "product claims" to garner consumer attention and focus; that is, companies may make specific statements or assertions on packaging regarding the product's characteristics or ability to perform certain functions. For example, a facial tissue manufacturer may promote its facial tissue as "the strongest tissue" or as "the most absorbent tissue" to concentrate consumer attention on their brand as opposed to a competitor's brand which is for sale in close proximity.

Because of the competitive nature of the marketplace, competitors consistently monitor one another's product claims to ensure that such claims represent truthful statements regarding the products. As such, it is imperative that companies compile appropriate data to substantiate product claims should such claims be challenged by one or more competitors. To meet this need for data and analysis of that data, companies routinely conduct studies, such as clinical studies, utilizing the consuming public as test subjects. As one might expect, these studies are typically carefully thought out and planned and generally utilize the assistance of one or more testing services to ensure appropriate, reliable data is gathered for analysis.

To date, some methods generally utilized by various companies to generate data to substantiate product claims have not been completely satisfactory. For example, methods used to date to measure the soothing characteristics of facial tissue, to allow direct comparison of the characteristics of different facial tissues, have been unsatisfactory for numerous reasons. Some of the shortcomings of these methods include the failure of the testing method to collect data from individuals with relevant skin damage, the failure of the testing method to collect data from skin on certain areas of the body, and the failure of the testing method to produce high confidence level, reproducible results. As such, a need exists in the art for methods for collecting data relating to measuring the soothing attributes of personal care compositions such as, for example, facial tissue.

SUMMARY OF THE INVENTION

The present invention is directed to methods for collecting data relating to one or more sensory attributes of a personal care composition. More specifically, the present invention is directed to methods for collecting data relating to the ability of a personal care composition, such as a facial tissue, or garment, to induce a soothing effect on damaged skin. The methods described herein allow data to be collected for various products and the data directly compared to determine the relative effectiveness of each product tested at inducing a soothing effect.

The methods described herein are in vivo methods which utilize sick or heathy test subjects, which may either be trained or untrained. In a preferred embodiment, the soothing attributes of facial tissue can be measured by first damaging the skin in a certain area by repetitive motion until a certain preset level of damage is achieved. This damage level is preferably assessed by the test subject. Following the induction of the damage, a contacting phase is initiated wherein the damaged skin is contacted with the test product followed by the subject rating the soothing attributes of the test product. This contacting phase typically comprises numerous cycles, with each cycle comprising a set amount of wipes. Preferably, the test subject rates the soothing attributes of the test product after each cycle of the contacting phase. This process allows for the rapid determining of soothing attributes of facial tissue while delivering skin damage in a product relevant manner.

Briefly, therefore, the present invention is directed to a method of measuring a sensory attribute of a personal care composition. The method comprises providing a product including a personal care composition and inducing an amount of damage onto an area of skin of a test subject. The damaged area of skin on the subject is contacted with the product to determine the amount of soothing of the personal care composition. Finally, the amount of soothing of the product is rated.

The invention is further directed to a method of measuring the soothing ability of a test facial tissue. The method comprises providing a test facial tissue and inducing damage onto a skin area around the nose of a test subject to a predetermined level. The damage is induced onto the skin area around the nose by repetitively wiping the skin area with an abrasive material. The level of damage on the skin is determined by the test subject. The test facial tissue is then contacted with the damaged area of skin on the subject to determine the amount of soothing of the test facial tissue. Finally, the amount of soothing of the test facial tissue is rated by the subject.

Other objects and features of this invention will be in part apparent and in part pointed out hereinafter.

Definitions

Within the context of this specification, each term or phrase below will include the following meaning or meanings.

"Soothing" refers to the perceived ability of a personal care composition to relieve or alleviate the perception of skin discomfort according to an individual's internal construct. Further, "soothing" or "soothes" refers to the ability of a personal care product to help irritated or dry skin feel better. Regarding personal care compositions, the terms "soothing," "calming," and "comforting" may be used interchangeably or in combination to refer to one or more attributes of the personal care composition.

"Test Product" refers to personal care compositions, substrates, formulations, materials, products or any portion of a product, or combination thereof, used during the conduct of a testing protocol.

"Damage Induction Phase" refers to the time period during the conduct of the study dedicated to damaging the subject's skin to a desired endpoint.

"Contacting Phase" refers to the time period during the conduct of the study dedicated to evaluating the test article for perceptual attributes and/or properties.

"Personal Care Products" includes personal care compositions or formulations, personal care substrates, and sensory modifiers, and any combinations thereof.

"Personal Care Compositions or Formulations" includes soaps, lotions, emulsions, mousses, balms, creams, washes, cleansing compositions, powders, oils, bath oils, aerosols, and compositions to be vaporized.

"Personal Care Substrates" includes woven, nonwoven, or knit webs or cloth, cellulose tissue bases webs, spun-bonded fabric, meltblown fabric, knit fabric, wet-laid fabric, scrims, needle-punched webs, hydroentangled webs, webs composed of synthetic fibers, webs composed of natural fibers, and combinations thereof. The webs may be either durable, semi-durable, or disposable. Personal care substrates include products such as facial tissue, bath tissue, paper towels, paper napkins, dry and wet wipes, infant diapers, child and adult incontinent products (liners, pads, and diapers), feminine care absorbent articles (liners, pads and pantiliners), cotton balls, swabs, or pads, adhesive and non-adhesive bandages and wound dressings.

"Sensory Modifiers" includes music, candles, fireplaces, pillows or other bedding, lighting, visual art, sachets or other potpourri.

"Sensory Response" refers to the measurement of an individual's internal construct of a perceptual attribute.

BRIEF DESCRIPTION OF THE DRAWINGS

FIG. 1 is a soreness visual analog scale suitable for recording data in accordance with the present invention.

FIG. 2 is a soothing visual analog scale suitable for recording data in accordance with the present invention.

DETAILED DESCRIPTION OF THE PREFERRED EMBODIMENTS

Figure 3:
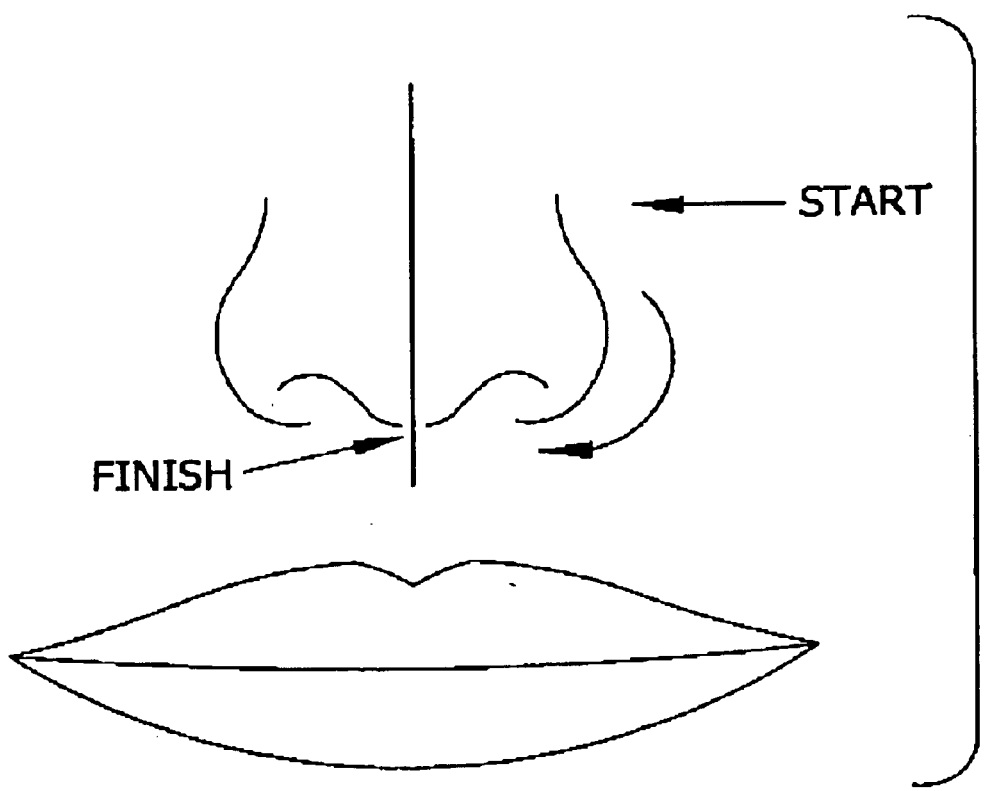
FIG. 3 is a diagram illustrating a wiping motion over a subject's nose in accordance with one method described herein.

In accordance with the present invention, it has been discovered that accurate, reliable data concerning the sensory attributes of personal care compositions, such as facial tissue, can be gathered utilizing methods described herein which comprise various testing steps. A wide variety of data, on a wide variety of products, can be obtained in a cost-effective manner while still providing consistent, reproducible results. The methods as described herein can generate data which consistently quantify sensory endpoints in clinical studies which leads to consistent and objective measurements of the sensory attributes of personal care compositions.

The present invention relating to methods for gathering and analyzing data concerning the attributes of a personal care compositions will be described herein in the context of the evaluation of the soothing attributes of a facial tissue. However, it should be recognized that numerous attributes of various consumer care compositions can be evaluated in accordance and within the scope of the present invention for their effect on skin or other epithelium. Exemplary personal care compositions suitable for evaluation in accordance with the present invention include facial tissue, bath tissue, paper towels, other non-woven materials such as various wipes, solids, skin care powders, emulsions, absorbent articles or portions thereof, creams, lotions, vapors, and solutions. It has been found that the methods described herein are particularly effective in gathering data related to the soothing attributes of facial tissue such that the soothing attributes, or lack thereof, can be compared to the soothing attributes of one or more other facial tissues or other types of products such as, for example, a paper towel or bath tissue. Additionally, the methods described herein are particularly effective in gathering data related to the soothing attributes of other wipes or personal care substrates.

The capability to quantify a facial tissue's calming or soothing attributes, or other perceptual attribute, when applied to irritated or damaged skin is essential for product claim support as generally discussed above. Additionally, this type of data is highly valuable in the development of improved products.

The methods described herein have a wide application for personal care compositions and can utilize a variety of test subjects, including both trained or untrained test subjects for evaluation of the soothing characteristics of the facial tissue utilizing psychophysical scales. Trained test subjects typically have been given instructional training on one or more specific evaluation scales and have a general understanding of scoring methods or protocol for these scales. Untrained test subjects are subjects that are naive to both the testing protocols and the testing scales. These subjects have not gone through specific training on how each sensory grade should feel, and simply utilize their own perception of what each grade is and how it should feel. Typically, untrained test subjects are consumers who may be recruited at a shopping mall, for example, and who simply bring their everyday experience to the table. In the methods of the present invention, it is generally preferred that untrained test subjects be utilized for evaluation of the personal care compositions.

Typically, the test subjects are pre-screened prior to evaluating the soothing characteristics of the facial tissue to ensure that a proper class of subjects is included in the evaluation. The methods of the present invention are suitable for use with both "healthy" or "sick" test subjects that are either "trained" or "untrained"; that is, the methods of the present invention can be utilized in combination with test subjects which exhibit no skin damage in the skin area to be tested (healthy subjects) as well as test subjects which exhibit pre-existing skin damage in the skin area to be tested, and either type of test subject may be trained or untrained.

For example, if the soothing attributes of a facial tissue are to be evaluated, test subjects may be either healthy subjects with no skin damage around the nose area, or may include test subjects with damaged skin around the nose area caused by, for example, having a cold or allergies and continuously wiping the area. In the present invention, it is preferred that the test subjects utilized be healthy. Because sick test subjects typically have varying degrees of soreness and damage in and around the nose area from irritants, wiping, and/or blowing their nose, utilizing healthy test subjects is preferred in the present invention as this allows the skin test area, typically around the nose area, to be damaged to a predetermined level, in a controlled fashion.

Several selection criteria for test subjects can be evaluated in order to select an appropriate group including sex, age, physical disorders, ability to understand instructions etc. For example, if the soothing characteristics of one or more facial tissues are being evaluated, in order to obtain the most reliable data, some subjects are typically excluded from testing employing the methods of the present invention.

Suitable exclusions may include: (1) subjects with visible skin diseases such as rashes which might interfere with evaluation of the test products; (2) subjects with abnormal pigmentation at or near the testing sites; (3) subjects with excessive dryness and/or redness at or near the testing sites; (4) subjects with atopic dermatitis and/or eczema at the test sites; (5) subjects taking medications which might interfere with the test results including any regimen of steroidal and/or non-steroidal anti-inflammatory drugs (including over the counter analgesics) or antihistamines; (6) subjects with a known hypersensitivity to facial tissues, cosmetic products, soaps, or lotions; (7) women who are pregnant or nursing; (8) current enrollment in a clinical study or subjects who have participated in a clinical study involving the test site within 1 week to 6 months, for example 180 days, 90 days, or 28 days prior to study irritation; (9) subjects that have consumed nicotine or caffeine within 2 to 12 hours, for example, 12 hours, 8 hours, or 4 hours, immediately prior to test product evaluation; (10) subjects that have consumed alcoholic beverages within 12 to 48 hours, for example, 48 hours, 36 hours, or 24 hours prior to the test product evaluation, etc. One skilled in the art will recognize that other factors may also be relevant in test subject evaluation, and may also be considered.

In accordance with the present invention, the evaluation of the soothing characteristics of a test product is initiated by damaging the area of skin to be tested in a damage induction phase. As one skilled in the art will recognize, the methods described herein can be applied to test various test products on various skin areas of the body. Although discussed primarily herein in the context of testing the soothing attributes of facial tissue on damaged skin around the nose, it will be recognized that any number of skin areas could be damaged and tested with numerous test products in accordance with the present invention. For example, where facial tissue is being evaluated, the skin area chosen to be damaged is typically the side of the nose, the nostril area, and the skin area between the nose and upper lip. Regarding the testing and analysis of facial tissue, this area of skin is the preferred area to be damaged as this is the skin area where the facial tissue is typically used to provide its intended function. Although typically less preferred, other areas of skin on the body can be damaged and evaluated within the scope of the present invention. As used herein, the term "damage" refers to the disruption of the barrier layer of skin that is often associated with the removal of a portion of the stratum corneum which can interrupt and degrade the barrier function of the skin. Typically, such damage will result in the skin area becoming red in color, irritated, and potentially dried out and flaking, as well as eliciting a negative sensory response.

The damage to the test area may be completed in numerous ways, including rubbing, wiping, or scraping the skin in the test area. In a preferred embodiment, a soreness inducing agent is wiped across the skin area to induce the skin damage. The soreness inducing agent provides the intended damage to the skin and includes, for example, an economy or low grade facial tissue, emory cloth, irritant, tape stripping, paper towel, cloth handkerchief, nonwoven materials, absorbent pads, bath tissue, liners, light grade sandpaper, other abrasive materials, and the like. Alternatively, damage can be caused by applying a chemical and/or biochemical irritant. Preferably, the soreness inducing agent is an economy or low grade facial tissue as this type of agent is reflective of how a consumer actually utilizes the facial tissue test product being evaluated. Further, it is preferred that the soreness inducing agent be at least slightly more abrasive than the test product being evaluated.

The damage introduced by the soreness inducing agent can be introduced by the subject, can be introduced by a technician, can be introduced by instruments, or can be introduced by a combination of the above; that is, the subject can wipe the agent across the skin area and/or a technician can perform the act and/or an instrument can perform the act. Preferably, the skin damage is introduced in a manner consistent with the normal, typical usage of the product being tested. For example, if a facial tissue is being evaluated, it is preferable that the damage be introduced by wiping a facial tissue over the skin area to be tested.

As mentioned above, the soreness inducing agent is wiped, rubbed, and/or applied to the test skin area to induce damage. The number of cycles utilized to induce the damage can vary. Likewise, the number of wipes per cycle can vary. Typically, the skin damage phase of the methods described herein consists of a predetermined number of possible cycles, with each cycle comprising the same predetermined number of wipes. Although once a cycle is initiated all of the wipes of that cycle are completed, once a subject reaches a predetermined level of skin damage, the cycles are discontinued, even if all potential cycles have not been completed. For example, in one embodiment the skin damage phase may comprise up to 15 cycles, with each cycle comprising 20 wipes with the soreness inducing agent (i.e., all 20 wipes on one side of the nose, or 10 wipes on each side of the nose). After the first cycle (i.e., after 20 wipes across the skin area with the soreness inducing agent), the level of soreness of the skin area is determined as discussed further below. If a predetermined damage level, or damage endpoint, of skin damage has been reached, the Damage Induction phase is complete and the subject moves on to the next phase. If the level of soreness of the skin area has not reached the damage endpoint, another damage inducing cycle is initiated and the process repeated. If at any time after a full cycle it is determined that the damage endpoint has been reached, the Damage Induction phase is complete and the subject moves on to the next phase. If, however, after the final cycle (cycle 15, for example) it is determined that the damage endpoint has not been reached, in some embodiments the subject is dismissed and no further evaluation is made.

The skin damage phase may include from about 1 cycle to about 1000 cycles, preferably from about 1 to about 250 cycles, more preferably from about 1 to about 100 cycles, more preferably from about 1 cycle to about 20 cycles, and more preferably from about 1 cycle to about 15 cycles with each cycle comprising from about 1 to about 1000 wipes, more preferably from about 1 to about 250 wipes, more preferably from about 1 to about 100 wipes, typically about 20 wipes. As one skilled in the art will recognize, the precise number of cycles and wipes per cycle is not critical, and may vary from one study to another, although it is preferred that the number of cycles, and wipes per cycle, remain constant throughout each independent study. Further, one skilled in the art will recognize that the wipes could be made on one side of the nose or both sides of the nose.

After the first cycle of the Damage Induction phase is complete, the subject, clinician, or instrument will measure or evaluate the amount of perceived damage (such as soreness) of the damaged skin area within a certain time of, for example, a few seconds. Generally, the subject is given a period of, for example, 5 seconds to about 1 minute during which a determination is made as to the amount of damage sustained. If it is determined that another damage cycle is required, the subject will usually be required to wait on the order of a few seconds to a few minutes between cycles. This wait period is typically preferred as it allows the damage introduced onto the test skin area to be fully appreciated by the subject prior to the initiation of a further damage cycle. Further, this wait period helps minimize the possibility of significantly overshooting the target amount of damage.

The damage endpoint, or predetermined limit, sought to be achieved by the damage inducing agent can be measured in numerous ways including sensory response, expert graded endpoints, or instrumental measures, or any combinations thereof. In one embodiment, a sensory endpoint based on psychophysical scales such as visual analog scores, questionnaires, magnitude estimation, or labeled dissimilarity scales is utilized to determine the amount of damage. In a preferred embodiment, a soreness visual analog scale can be utilized. In this embodiment, the subject utilizes his/her own personal perception of soreness level based on the damage inducing cycles and provides feedback to a technician via marking a hashmark on a soreness continuum to indicate the soreness level attained at a given point in the damage introduction phase. With this approach, a soreness scale is utilized and when a subject indicates on the scale (via the hashmarking) that a certain soreness has been reached (the damage endpoint), the damage introduction phase is complete. For example, a soreness scale of from 0 (No soreness) to 3 (extremely sore) can be utilized, wherein a score of 1 indicates slightly or mildly sore and 2 indicates moderately sore. If the desired damage endpoint for the study is set at a damage level of 2 or greater (that is, all test subjects will move to the next phase of the study once the damage endpoint of 2 or greater is reached), the cycles as discussed above are continued until the subject indicates that the soreness level has reached a 2 or greater. At this level, the intended damage level has been achieved and no further damage is introduced. As mentioned above, if all cycles are completed and a damage level of 2 or greater is never attained, the subject may be dismissed. A suitable soreness visual analog scale is shown in FIG. 1. This is a preferred embodiment for measuring the damage endpoint as each test subject provides a subjective, personal perception of the soreness and/or discomfort level allowing the damage endpoint to be correlated to an undesirable neurosensory value as reported by the subject.

In an alternative embodiment, the damage endpoint can be measured by an expert grader utilizing an erythema scale, redness scale, or similar type scale. Typically, the expert grader has received prior, extensive training in grading skin damage to a certain area on a particular scale, and has acquired the required skills to consistently grade a particular level of skin damage in a particular area. The expert grader will monitor the damage being induced onto the appropriate skin area and after each cycle of the damage inducing phases will rate the damage based upon a visual irritation scoring method. This allows the damage on the skin area to be increased gradually over a period of time and reduces the chance of the damage endpoint being surpassed such that the subject must be excluded from the trial. For example, if the damage endpoint is set at a seven on a scale of 0 (no damage) to 10 (extreme damage), the expert grader will grade the damage after each cycle until a damage level of 7 is reached in the expert's opinion. Once this damage endpoint is reached, the Damage Induction phase is complete and the subject is moved to the next phase of the study. Although the test subject does not provide subjective feedback, this method can be effective and accurate.

In a further alternative embodiment, the damage endpoint can be measured utilizing an instrumental endpoint. In this embodiment, an instrument or tool is utilized to mechanically monitor and measure the damage being introduced on the appropriate skin area. Suitable instruments for use in this embodiment include, but are not limited to, chromometers, conductance instruments, evaporimeters, FTIR, and NMR. In one preferred embodiment, an appropriate probe can be utilized to measure the trans-epidermal water loss (TEWL) from the desired area of skin. The probe is first utilized to measure how much moisture is leaving the epidermal layer of skin as a function of time prior to the introduction of any damage with the damage inducing tissue to set the baseline. After the baseline has been determined, the damage cycle(s) is initiated and the probe measures how much water is lost from the epidermal layer of skin over the course of the cycles. Once the predetermined level of water has been lost from the epidermal layer (i.e., two times, three times, four times, etc. the baseline) the appropriate amount of damage has been introduced onto the desired area and the Damage Induction phase is complete.

After the damage endpoint has been reached, the facial tissue being evaluated is applied to the damaged skin area in Contacting Phase. Similar to the introduction of the damage via the damage inducing agent, the test products can be contacted with the damage skin area by the test subject, by a technician, by an instrument or by a combination thereof. Typically, it is preferred that the subject contact the test product with the damaged skin area so that the article is utilized in a manner consistent with how a typical consumer would utilize it (i.e., motion, pressure, etc.).

Similar to the damage introduction phase discussed above, the contacting of the test product with the damaged skin area is typically completed in cycles, with each cycle comprising a set number of wipes. For example, the contacting with the test product phase may comprise from about 1 to about 100 cycles or more, typically from about 1 to about 20 cycles, and more typically from about 6 to about 12 cycles. The number of wipes per cycle may be from about 1 to about 100 or more, and is typically from about 5 to about 10 or so. A preferred test product contacting phase may comprise, for example, 12 cycles with each cycle comprising 5 wipes. Once a specified cycle is complete, the subject is typically given a few seconds to a minute to record the perceptual attribute, such as soothing level, as described below before the next contacting cycle is initiated. Although longer periods can be utilized, it is preferred that the wait before recording the soothing level be on the order of a few seconds. Unlike the Damage Induction phase discussed above, each test subject during the test product contacting phase completes each of the cycles in this part of the trial.

Once the first cycle of the Contacting Phase is complete, the test subject, typically after a short pause, is asked to rate or score the soothing attributes of the test facial tissue. One method that can be utilized for the scoring of the soothing attributes of the facial tissue is a visual analog soothing scale. In some embodiments, a soothing visual analog scale is used that may start with zero (not soothing) and ends with a higher number, such as 3 (very soothing), for example. A suitable soothing visual analog scale for use in accordance with the present invention is shown in FIG. 2. In this example, the number 1 may represent mildly soothing and the number 2 may represent moderately soothing. After each independent cycle, a soothing visual analog scale is presented to the test subject. Typically, a new, unmarked soothing visual analog scale is utilized after each cycle, although it is within the scope of the present invention to utilize the same soothing visual analog soothing scale or multiple copies of the visual analog soothing scale on the same page throughout all contacting cycles. Alternatively, electronic or other means of data collection can be utilized. The soothing visual analog scale may be, for example, in the form of a continuum from 0 to 3, and the test subject is asked to put a hashmark along the line which corresponds to the level of soothing the subject received from contacting the test product with the damaged skin during the previous contacting cycle; that is, the test subject can mark anywhere on the line range and does not necessary have to mark on the position of the line which corresponds to a whole number.

When utilizing a soothing visual analog scale, the numbering on the scale is not critical, but typically starts at zero (which indicates no soothing) and ends with a higher number, such as 3. In this example, what is measured and ultimately utilized for statistical analysis is the length of the line on the scale from 0 (not soothing) to the hashmark introduced onto the line by the test subject after each cycle is complete. The length of this line is representative of the perceived soothing attribute of the test facial tissue. For example, the soothing visual analog scale shown in FIG. 2 begins at 0 and ends with 3, and has a length of 7.5 centimeters. If, after the first cycle the test subject put a hash mark directly above the number 1, the length of the line used for analysis (to determine the amount of soothing) would be 2.5 centimeters (7.5/3=2.5). Stated another way, it is not critical where the hash marks are introduced onto the continuum per se, but what is critical is the length of the line as measured from zero to the hashmark.

In an alternative embodiment, the soothing attributes of the test product can be rated by the test subject utilizing preference scoring. With this method, the test subject actually compares two or more different test products and determines which provides more soothing, or whether each test product provides the same amount of soothing. This rating system can be used when two different skin areas are damaged, such as both sides of a nose, such that one test product is contacted with one damage area and the second test product is contacted with the second damaged area. After the contacting, the test subject decides which test product provided more soothing. Alternatively, two separate test products can be wiped over the same damaged skin area and compared. This type of rating system provides clear cut data of a direct comparison of two different test products.

In a further alternative embodiment, the soothing attributes of the test product can be rated by the test subject utilizing magnitude estimation. In this embodiment, quantifiable data is provided by the test subject by asking the subject, after the Damage Induction phase but prior to the Contacting phase, to pick a number describing the amount of soreness on the damaged area of skin. The number is chosen by the subject, without any scales or guidance by the technician. After the number is chosen, the first cycle of the Contacting phase is completed followed by again asking the subject to pick a number to describe the amount of soreness on the damaged skin area. The difference, or magnitude, between the first number and the second number may be utilized for analysis to determine the soothing attributes of the test product. It will be recognized by one skilled in the art that other methods of analysis are available. The remaining cycles in the contacting phase are completed in a similar manner.

In a still further alternative embodiment, the soothing attributes of a test product can be rated and collected utilizing electronic means. Additionally, electronic means of rating and collecting data can be used in combination with one or more of the methods described herein.

Regardless of what rating approach is utilized, after the first cycle is complete and the subject has provided the rating, each additional Contacting phase is completed followed by a rating after each cycle until all cycles have been completed along with the different ratings. For example, if the methods being employed comprise 12 Contacting phase cycles, with each cycle comprising 5 wipes, the subject would provide 12 different ratings, or one rating after each cycle. As such, after cycle 1 (5 wipes), the first rating is provided; after cycle 2 (10 total wipes, 5 from the first cycle and 5 from the second cycle) the second rating is provided; after cycle 3 (15 total wipes), the third rating is provided, etc., for a total of 12 ratings. The soothing data compiled from the ratings by the test subject after each cycle are used to determine the relative soothing capabilities of test products such as facial tissue.

Typically, the methods described herein are utilized to compare the soothing attributes of one facial tissue to that of a second facial tissue. As one skilled in the art will recognize, the methods described herein can also be utilized to compare more than two products that are similar or dissimilar as well. For example, the methods described herein can be utilized to compare the soothing attributes of three or four or more facial tissues in a single study. In one embodiment of the present invention, the same test subjects are utilized to compare one test facial tissue to another; that is, a test subject will test both test facial tissues within a prescribed period of time such that data gathered from the use of both test products can be analyzed and compared. Alternatively, in a less preferred embodiment, one set of test subjects can test one test facial tissue while a second set of test subjects, utilizing the same procedure, can test a second test facial tissue and the data from both collected and analyzed.

In the embodiment where the test subjects test both facial tissues for comparison, it is typically preferred that there be some type of recovery period between the testing of the first test facial tissue and the testing of the second. For example, there may a 24 hour recovery period between the testing of the first facial tissue and the second. This recovery period allows the damaged skin area to recover prior to additional testing. The recovery period can be any period sufficient for the damaged skin area to partially recover, and can be, for example, from a few hours to many days or weeks.

The soothing data collected from the methods described herein, such as the measurement of the line lengths from the soothing visual analog scales described above, is collected and analyzed utilizing statistical analysis methods well known to those skilled in the art to produce p-values and graphical representations of soothing characteristics of the facial tissue. For example, the soothing response data may be analyzed to calculate the mean data point for each cycle (that is, the mean soothing visual analog scale line length) and repeated measures analysis of variance utilized to compare the mean soothing data for each test product evaluated. This data allows for direct comparison of the soothing attributes of multiple facial tissues.

Additionally, other statistical and data analysis models may be utilized to provide meaningful data including, for example, effects for the technicians utilized, subject differences, maximum irritation score and time that the maximum irritation was achieved. Further, analysis can be done to determine whether the soothing data varied by day, test session, etc. For purposes of the examples used herein, p-values of less than 0.05 are used to indicate a statistically significant difference.

The present invention is illustrated by the following example which is merely for the purpose of illustration and is not to be regarded as limiting the scope of the invention or manner in which it may be practiced.

EXAMPLE

In this example, the soothing attributes of Kleenex® facial tissue and Kleenex® Lotion facial tissue were analyzed and compared to determine which facial tissue imparted more soothing when contacted with damaged nose skin.

Two separate groups of 20 test subjects were recruited for the testing of the facial tissues. Four technicians were utilized to administer the testing and record the results. The test subjects were recruited based upon the following criteria: Inclusions: (1) Age 18 to 60 in good general health; (2) Free of systemic disorder; (3) Ability to understand and provide written informed consent; (4) Ability to complete the course of study and to comply with instructions; (5) Ability to arrive for testing without cologne, perfume, after-shave lotion, or any other topical facial products (lip and eye makeup acceptable); (6) Ability to refrain from using over the counter analgesics, antihistamines, and/or nasal sprays for 12 hours before each visit; Exclusions: (1) Individuals with any visible skin disease or rash which may interfere with the evaluations; (2) Individuals experiencing nasal discharge and/or a sore nose or who have had nasal discharge and/or a sore nose within the seven days prior to the evaluations; (3) Individuals with abnormal skin pigmentation at test site; (4) Individuals with excessive dryness and/or redness at test site; (5) Individuals with active atopic dermatitis and/or eczema at the test site; (6) Individuals taking medications which might interfere with the test results, including any regimen of steroidal and/or non-steroidal anti-inflammatory drugs including over the counter analgesics or antihistamines; (7) Individuals with a known hypersensitivity to facial tissues, cosmetic products, soaps, or lotions; (8) Women who are pregnant or nursing; (9) Individuals currently enrolled in a clinical study or who have participated in a clinical study involving the test site within 28 days prior to this study; (10) Individuals that have consumed nicotine or caffeine within the four hours immediately prior to the facial tissue evaluation; (11) Individuals that have consumed alcoholic beverages within 24 hours prior to the facial tissue evaluation; (12) Individuals who are employees of a consumer products company or marketing research company; and (13) Individuals who have participated in a study using a facial tissue soothing protocol.

A quarter folded economy facial tissue (soreness inducing tissue) was wiped by a technician on one side of the test subject's nose and then on the other in a repetitive manner. The technician began by wiping the left side of the nose with the soreness inducing tissue five times. The wiping was done in a downward motion starting immediately above the nasolabial fold, moving down along the nasolabial fold, under the anterior aspect of the naris, and terminated at the bridge of the nose. A diagram of this wiping motion is shown in FIG. 3. Following the five consecutive wipes to the left side of the nose, the technician unfolded the soreness inducing tissue to the half fold and folded it again in the opposite direct to expose two new surfaces. After refolding, the technician proceeded to wipe the right side of the nose five times in the same manner. The technician then discarded the soreness inducing tissue, selected a new soreness inducing tissue, and repeated the cycle of five wipes on each side of the nose for a total of twenty wipes (ten wipes on each side of nose). This twenty repetitive wipes constituted one wiping cycle.

Fifteen seconds (±3 seconds) after the conclusion of the wiping cycle, the test subject was given a soreness visual analog scale as shown in FIG. 1 and asked to place a hash mark anywhere along the scale (scale=7.5 centimeters in length) that best represented the degree of soreness they were experiencing after the wiping cycle. After five minutes (±30 seconds) elapsed from the end of the previous wiping cycle, the technician repeated the wiping process in a new wiping cycle as described above. Wiping cycles and soreness visual analog scoring was repeated as described above until such time that the test subject reported a soreness visual analog scale score greater than or equal to 2.0 (5.0 centimeters).

Once a soreness visual analog score of 2.0 or more was achieved, the sore nose state (damage endpoint) was considered established and the repetitive wiping discontinued. The test subject was asked to change rooms and proceeded to the next phase of the study, which included the evaluation of the soothing attributes of the test products (Kleenex® Facial Tissue and Kleenex® Lotion Facial Tissue). In the event that the desired soreness score was not obtained after fifteen wiping cycles, the subject was dismissed from the study.

Test subjects began the evaluation of the test product five minutes (±30 seconds) after they had achieved the sore nose state. During the five minutes prior to evaluation of the test product, the test subjects were instructed on how to wipe their nose with the test product. This instruction consisted of telling the test subject that they, instead of the technician, would be performing the wiping this part of the evaluation, and that they could wipe their nose as they normally would, being sure to make contact with the area wiped during the first phase of the study. Additionally, the soothing visual analog scale utilized, shown in FIG. 2, was discussed with, and explained to, each test subject. No definition of soothing was given to the test subjects.

The technician dispensed to the test subject a first test product from an unbranded, coded, tissue box out of sight of the test subject. The test subject wiped the test product on both sides of their nose making contact with the area previously wiped to induce soreness. In this phase of the study, one wiping cycle consisted of 5 wipes. Following the 5 wipes with the test product, the test subject discarded the facial tissue and after 15 seconds (±3 seconds) and was given one soothing visual analog scoring sheet with which to rate the soothing attributes of the test product in a similar manner to rating the soreness as discussed above. Again, the test scale was 7.5 centimeters and the test subject was asked to place a hash mark at the appropriate place on the line which corresponded to the amount of soothing felt. This hash mark was used for analysis of the soothing attributes of the test product.

After the test subject had rated the soothing attributes of the test product, the technician collected the marked scoring sheet and provided the subject with a new test product as described above. After 6 wiping cycles the test subject changed rooms and underwent an additional 6 wiping cycles for a total of twelve wiping cycles each comprised of 5 wipes. The test subject evaluated the same test product during all 12 wiping cycles. A new, unmarked soothing visual analog scale was used after each cycle.

Following the evaluation of the first test product, the test subjects underwent a nose recovery period before evaluating the second test product to allow comparison of the first test product and the second test product. During the test subject's second visit, the introduction of the sore nose state and the evaluation of the second test product was performed in an identical fashion as in their first visit. The order of test product evaluation was randomized according to a randomization schedule which can easily be prepared by one skilled in the art. The nose recovery period for one half of the subjects (cell 1) was 24 hours (±60 minutes) and 7 days (±60 minutes) for the second half (cell 2) of the test subjects.

Figure 4:
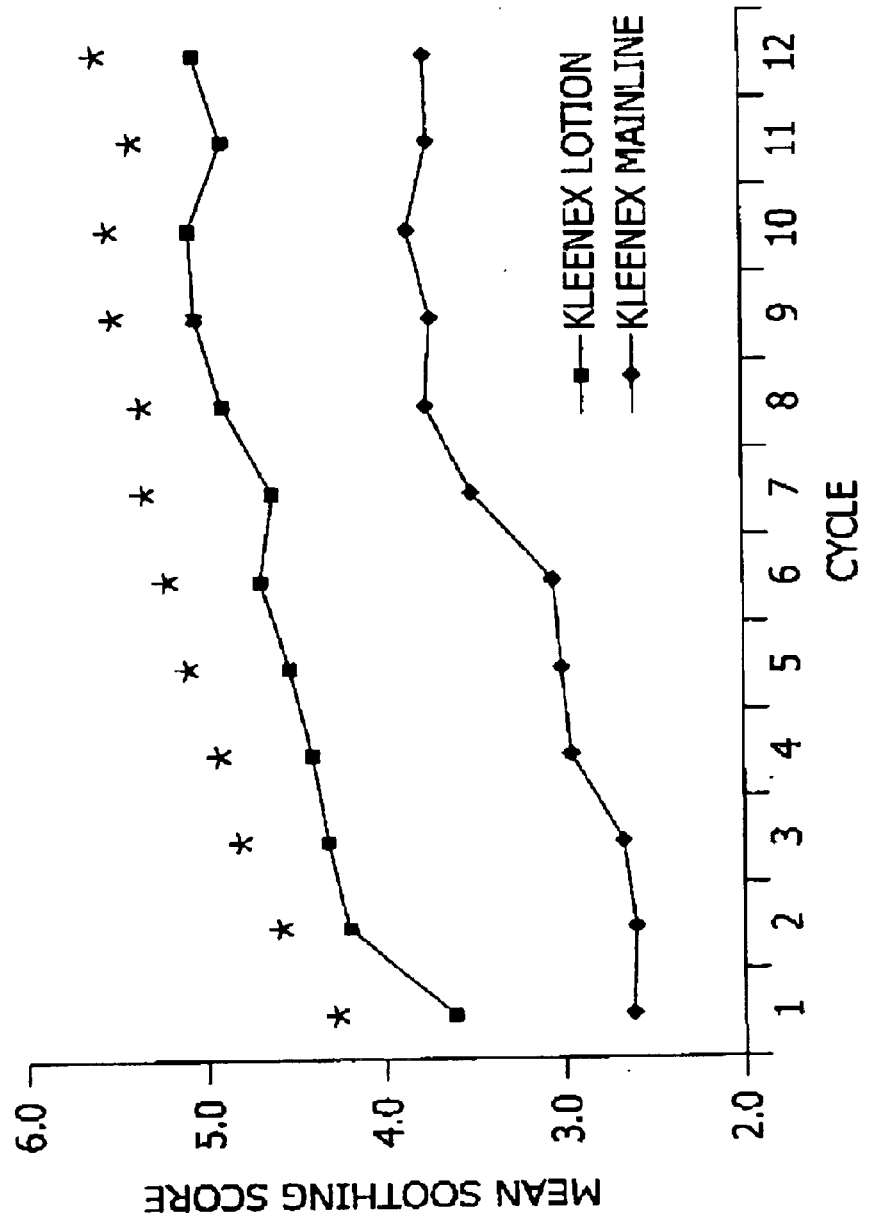
FIGS. 4 and 5 are graphs illustrating soothing data acquired in Example 1 herein.
Figure 5:
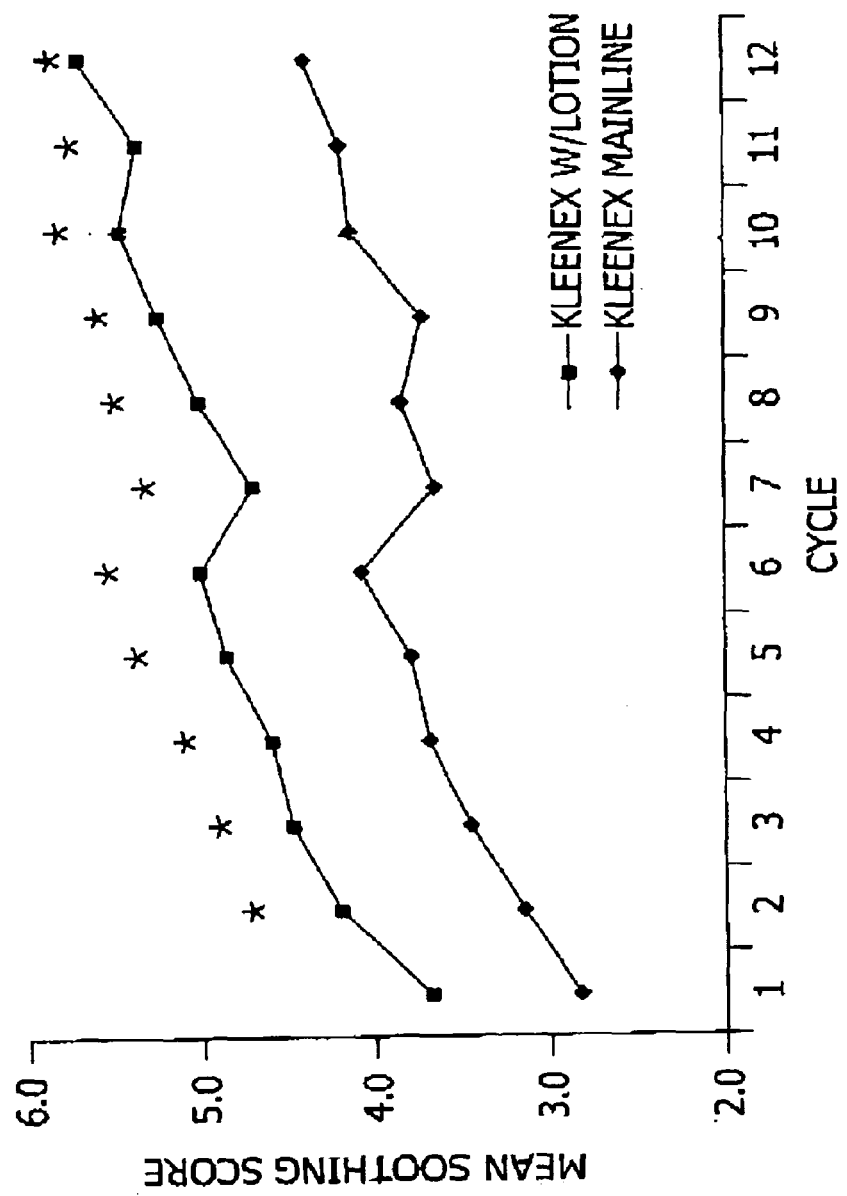

The results of the 24 hour and 7 day soothing studies are shown in FIGS. 4 and 5, respectively. Repeated measures analysis of variance was used to compare and analyze the mean soothing response for each test product evaluated to determine whether a statistically significant difference in responses was noted. P-values of less than 0.05 indicate a statistically significant difference. These results are set forth in Tables 1a and 1b and 2a and 2b:

TABLE 1a

Mean soothing scores by cycle For 24 Hour Soothing Study

| Code | Cycle 1 | Cycle 2 | Cycle 3 | Cycle 4 | Cycle 5 | Cycle 6 | Cycle 7 | Cycle 8 | Cycle 9 | Cycle 10 | Cycle 11 | Cycle 12 | Overall |
|---|---|---|---|---|---|---|---|---|---|---|---|---|---|
| Kleenex Mainline | 2.60 | 2.59 | 2.67 | 2.95 | 3.00 | 3.05 | 3.50 | 3.75 | 3.72 | 3.84 | 3.73 | 3.74 | 3.26 |
| Kleenex Lotion | 3.59 | 4.18 | 4.30 | 4.39 | 4.51 | 4.67 | 4.60 | 4.88 | 5.04 | 5.07 | 4.89 | 5.04 | 4.60 |
| p-value | .0040 | .0001 | .0002 | .0011 | .0016 | .0006 | .0046 | .0060 | .0021 | .0121 | .0262 | .0243 | .0002 |

Table 1b: Mean soothing scores by cycle For 7 Day Soothing Study

TABLE 1b

Mean soothing scores by cycle For 7 Day Soothing Study

| Code | Cycle 1 | Cycle 2 | Cycle 3 | Cycle 4 | Cycle 5 | Cycle 6 | Cycle 7 | Cycle 8 | Cycle 9 | Cycle 10 | Cycle 11 | Cycle 12 | Overall |
|---|---|---|---|---|---|---|---|---|---|---|---|---|---|
| Kleenex Mainline | 2.80 | 3.13 | 3.43 | 3.67 | 3.77 | 4.07 | 3.64 | 3.84 | 3.72 | 4.13 | 4.20 | 4.41 | 3.74 |
| Kleenex Lotion | 3.63 | 4.18 | 4.46 | 4.58 | 4.84 | 5.00 | 4.70 | 5.02 | 5.27 | 5.48 | 5.39 | 5.73 | 4.86 |
| p-value | .1239 | .0223 | .0075 | .0079 | .0120 | .0266 | .0067 | .0024 | .0004 | .0004 | .0012 | .0040 | .0008 |

As FIGS. 4 and 5, and Tables 1a and 1b indicate, a statistically significant difference was noted between the test products evaluated and it was determined that Kleenex Lotion facial tissue imparted more soothing attributes than did Kleenex facial tissue.

In view of the above, it will be seen that the several objects of the invention are achieved. As various changes could be made in the above-described methods without departing from the scope of the invention, it is intended that all matter contained in the above description be interpreted as illustrative and not in a limiting sense.

What is claimed is:

1. A method of measuring the soothing ability of a test facial tissue, the method comprising:
   (a) providing a test subject;
   (b) performing a skin damage induction phase including:
      (1) providing an abrasive material for inducing damage to a skin area around the nose of the test subject;
      (2) predetermining an amount of damage to be induced onto the skin area; and
      (3) using the abrasive material to induce damage onto the skin area utilizing a damage inducing cycle
      (4) determining the level of damage on the area of skin induced by the abrasive material by the test subject after the damage inducing cycle;
      (5) repeating steps (b3) and (b4) until the test subject determines that the predetermined level of damage has been induced;
   (c) performing a contacting phase including:
      (1) providing a test facial tissue;
      (2) contacting the damaged area of skin with the test facial tissue including wiping the test facial tissue on the damged area of skin utilizing at least one contacting cycle; and
      (3) rating the amount of soothing of the test facial tissue by the test subject after each contacting cycle.

2. The method as set forth in claim 1 wherein the test subject is a healthy test subject.

3. The method as set forth in claim 1 wherein the test subject is a sick test subject.

4. The method as set forth in claim 1 wherein the contacting of the damaged area of skin with the test facial tissue comprises from about 1 to about 12 contacting cycles.

5. The method as set forth in claim 4 wherein the contacting cycles comprise wiping the test facial tissue on the damaged area of skin from about 1 to about 5 times.

6. The method as set forth in claim 5 wherein the amount of soothing of the test facial tissue is rated by the test subject after each contacting cycle utilizing a visual analog scale.

7. The method as set forth in claim 1 wherein the damage is induced onto the skin area around the nose utilizing from about 1 up to about 15 damage inducing cycles.

8. The method as set forth in claim 7 wherein the damage inducing cycle comprises repetitively wiping the skin area with the abrasive material, and wherein the repetitive wiping during the damage inducing cycle is done by a technician.

9. The method as set forth in claim 8 wherein each damage inducing cycle comprises from about 1 to about 10 wipes.

10. The method as set forth in claim 7 wherein the damage on the skin area around the nose is determined by the test subject after each damage inducing cycle utilizing a visual analog scale.

11. The method as set forth in claim 10 wherein the damage inducing cycles continue until the predetermined amount of damage on the skin area around the nose has been attained based on the ratings by the test subject on the visual analog scale.

12. A method of measuring the soothing ability of a test facial tissue, the method comprising:
  (a) providing a test subject;
  (b) performing a skin damage inducing phase including:
    (1) providing an abrasive material for inducing damage to a skin area around the nose of the test subject;
    (2) predetermining an amount of damage to be induced onto the skin;
    (3) using the abrasive material to induce damage onto the skin area utilizing from about 1 to about 15 damage inducing cycles, each damage inducing cycle comprising repetitively wiping the skin area around the nose of the test subject with an abrasive material, each damage inducing cycle comprising from about 1 to about 10 wipes, the wiping being done by a technician;
    (4) determining the level of damage on the area of skin induced by the abrasive material by the test subject after each damage inducing cycle utilizing a visual analog scale;
    (5) repeating steps (b3) and (b4) until the test subject determines that the predetermined level of damage has been induced;
  (c) performing a contacting phase including:
    (1) providing a test facial tissue;
    (2) contacting the test facial tissue with the damaged area of skin around the nose of the test subject to determine the amount of soothing of the test facial tissue, the contacting comprising from about 1 to about 12 contacting cycles, each contacting cycle comprising wiping the test facial tissue on the damaged area of skin from about 1 to about 5 times, the contacting of the test facial tissue being done by the test subject;
    (3) rating the amount of soothing of the test facial tissue by the test subject after each contacting cycle utilizing a visual analog scale; and
  (d) compiling the data generated by the test subject during the contacting cycles from the visual analog scale.

13. The method as set forth in claim 12 wherein the abrasive material is an economy facial tissue.

14. The method as set forth in claim 12 wherein the test subject is a healthy test subject.

15. The method as set forth in claim 12 wherein the test subject is a sick test subject.

* * * * *